US00PP17793P2

(12) United States Plant Patent
Litton

(10) Patent No.: US PP17,793 P2
(45) Date of Patent: Jun. 12, 2007

(54) ***PHLOX* PLANT NAMED 'DAVID'S LAVENDER'**

(50) Latin Name: *Phlox paniculata*
Varietal Denomination: David's Lavender

(75) Inventor: Kathryn Litton, Blairsville, GA (US)

(73) Assignee: Itsaul Plants, Alpharetta, GA (US)

( * ) Notice: Subject to any disclaimer, the term of this patent is extended or adjusted under 35 U.S.C. 154(b) by 60 days.

(21) Appl. No.: 11/223,869

(22) Filed: Sep. 8, 2005

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Phlox* plant named 'David's Lavender', characterized by its upright plant habit; columnar plant form; vigorous growth habit; large inflorescences with numerous lavender-colored flowers; long flowering period; good garden performance; and resistant to Powdery Mildew.

2 Drawing Sheets

Botanical designation: *Phlox paniculata.*
Cultivar denomination: 'David's Lavender'.

BACKGROUND OF THE INVENTION

The present Invention relates to a new and distinct cultivar of *Phlox* plant, botanically known as *Phlox paniculata,* and hereinafter referred to by the cultivar name David's Lavender.

The new *Phlox* is a naturally-occurring branch mutation of the *Phlox paniculata* cultivar David, not patented. The new *Phlox* was discovered and selected by the Inventor as a flowering branch of a plant of 'David' in a controlled environment in Blairsville, Ga.

Asexual reproduction of the new cultivar by cuttings at Dahlonega, Ga. since March, 2003, has shown that the unique features of this new *Phlox* are stable and reproduced true to type in successive generations.

SUMMARY OF THE INVENTION

Plants of the cultivar David's Lavender have not been observed under all possible environmental conditions. The phenotype may vary somewhat with variations in environment such as temperature and light level without, however, any variance in genotype.

The following traits have been repeatedly observed and are determined to be the unique characteristics of 'David's Lavender'. These characteristics in combination distinguish 'David's Lavender' as a new and distinct cultivar of Phlox:

1. Upright plant habit; columnar plant form.
2. Vigorous growth habit.
3. Large inflorescences with numerous lavender-colored flowers.
4. Long flowering period.
5. Good garden performance.
6. Resistant to Powdery Mildew.

Plants of the new *Phlox* can be compared to plants of the parent, the cultivar David. Plants of the new *Phlox* differ from plants of the cultivar David primarily in flower color as plants of the cultivar David have white-colored flowers.

Plants of the new *Phlox* can be compared to the *Phlox* cultivar Barfourteen, disclosed in U.S. Plant Pat. No. 12,605. In side-by-side camparisons, plants of the new *Phlox* differed from plants of the cultivar Barfourteen in the following characteristics:

1. Plants of the new *Phlox* were more vigorous than plants of the cultivar Barfourteen.
2. Plants of the new *Phlox* had longer internodes and were not as dense and bushy as plants of the cultivar Barfourteen.
3. Plants of the new *Phlox* had slightly larger flowers than plants of the cultivar Barfourteen.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Phlox.*

The photograph on the first sheet comprises a side perspective view of a typical flowering plant of 'David's Lavender' grown in an outdoor nursery.

The photograph on the second page is a close-up view of a typical inflorescence of 'David's Lavender'. Plants used in the photographs were about one year old.

DETAILED BOTANICAL DESCRIPTION

The following observations and measurements describe plants grown in Dahlonega, Ga. in a polyethylene-covered greenhouse and under commercial production practices during the spring and summer. Plants were grown in one-gallon containers and were about one year old when description was taken. During the production of the plants, day temperatures ranged from 16° C. to 35° C. and night temperatures ranged from 13° C. to 24° C. In the following description, color references are made to The Royal Horticultural Society Colour Chart, 1995 Edition, except where general terms of ordinary dictionary significance are used.

Botanical classification: *Phlox paniculata* cultivar David's Lavender.

Parentage: Naturally-occurring branch mutation of the *Phlox paniculata* cultivar David, not patented.

Propagation:

*Type.*—By cuttings.

*Time to initiate roots, summer.*—About three weeks at 29° C.

*Time to initiate roots, winter.*—About four weeks at 24° C.

*Time to produce a rooted plant, summer.*—About 6.5 weeks at 29° C.

*Time to produce a rooted plant, winter.*—About 8.5 weeks at 24° C.

*Root description.*—Thick, fleshy; white in color.

*Rooting habit.*—Freely branching.

Plant description:

*Plant form/habit.*—Upright plant habit; columnar form; vigorous growth habit. Freely branching habit, about seven basal branches per plant.

*Plant height.*—About 51 cm.

*Plant width (spread).*—About 38 cm.

*Lateral branches.*—Length: About 41 cm. Diameter: About 4 mm. Internode length: About 3.8 cm. Strength: Strong. Texture: Smooth, glabrous. Color: 144A.

*Foliage description.*—Arrangement: Opposite, simple; sessile. Length: About 9.8 cm. Width: About 2.9 cm. Shape: Lanceolate. Apex: Sharply acute to acuminate. Base: Attenuate. Margin: Entire. Texture, upper and lower surfaces: Smooth, glabrous. Venation pattern: Pinnate. Color: Developing and fully expanded leaves, upper surface: Close to 147A; venation, close to 146A. Developing and fully expanded leaves, lower surface: Close to 147B; venation, similar to lamina.

Flower description:

*Flower type/habit.*—Single, rounded salverform flowers arranged in large rounded panicles; flowers pinwheel in shape with nonimbricate petals. Flowers face upright and outward. Freely flowering habit; one inflorescence per branch; each inflorescence with about 55 flowers.

*Fragrance.*—Faint; sweet and fresh.

*Natural flowering season.*—Long flowering period; continuously flowering throughout the summer in Pennsylvania.

*Postproduction longevity.*—Flowers last about one week on the plant. Flowers persistent.

*Inflorescence height.*—About 9.8 cm.

*Inflorescence diameter.*—About 6.5 cm.

*Flower buds.*—Height: About 2 cm. Diameter: About 4 mm. Shape: Elongated oblong. Color: Close to 144A.

*Flowers.*—Diameter: About 2.5 cm. Depth: About 2.3 cm. Throat diameter: About 4 mm. Tube length: About 2.2 cm. Tube diameter, base: About 2 mm.

*Petals.*—Quantity per flower: Typically five in a single whorl; petal nonimbricate; petals fused at the base into a narrow tube. Lobe length: About 1.1 cm. Lobe width: About 1.1 cm. Lobe shape: Obovate to spatulate. Lobe apex: Rounded. Lobe margin: Entire. Aspect: Mostly flat. Texture, lobes, upper and lower surfaces: Smooth, glabrous. Color: Developing and fully expanded petals, upper surface: Close to 155D overlain with close to 80A; towards the base, close to 155D; faint central stripes and ring at throat, close to 80A. Developing and fully expanded petals, lower surface and tube: Close to 155D blushed with close to 80A. Throat: Close to 155D.

*Sepals.*—Quantity per flower: Typically five in a single whorl, fused; narrow tubular calyx. Length: About 9 mm. Width: About 2 mm. Shape: Lanceolate. Apex: Sharply acuminate. Margin: Entire. Texture, upper and lower surfaces: Smooth, glabrous. Color, upper and lower surfaces: Close to 144A.

*Pedicels.*—Length: About 5 mm. Diameter: About 1.5 mm. Angle: Erect to about 60° from vertical. Texture: Smooth, glabrous. Color: Close to 144A.

*Reproductive organs.*—Stamens: Quantity per flower: Typically five adnate to flower throat. Filament color: Close to 155D. Anther shape: Linear, elongated. Anther length: About 2 mm. Anther diameter: Less than 1 mm. Anther color: Close to 9A. Pollen amount: Moderate. Pollen color: Close to 9A. Pistils: Quantity per flower: Typically one. Pistil length: About 2.5 cm. Stigma shape: Tri-parted. Stigma color: Close to 155D. Style length: About 2.4 cm. Style color: Close to 145D. Ovary color: Close to 144A.

*Seed/fruit.*—Seed and fruit development have not been observed.

Disease/pest resistance: Plants of the new *Phlox* have been observed to be resistant to Powdery Mildew. Plants of the new *Phlox* have not been noted to be resistant to pests and other pathogens common to *Phlox*.

Garden performance: Plants of the new *Phlox* have been observed to have good garden performance and tolerate rain, wind and temperatures ranging from −23° C. to 38° C.

It is claimed:

1. A new and distinct cultivar of *Phlox* plant named 'David's Lavender', as illustrated and described.

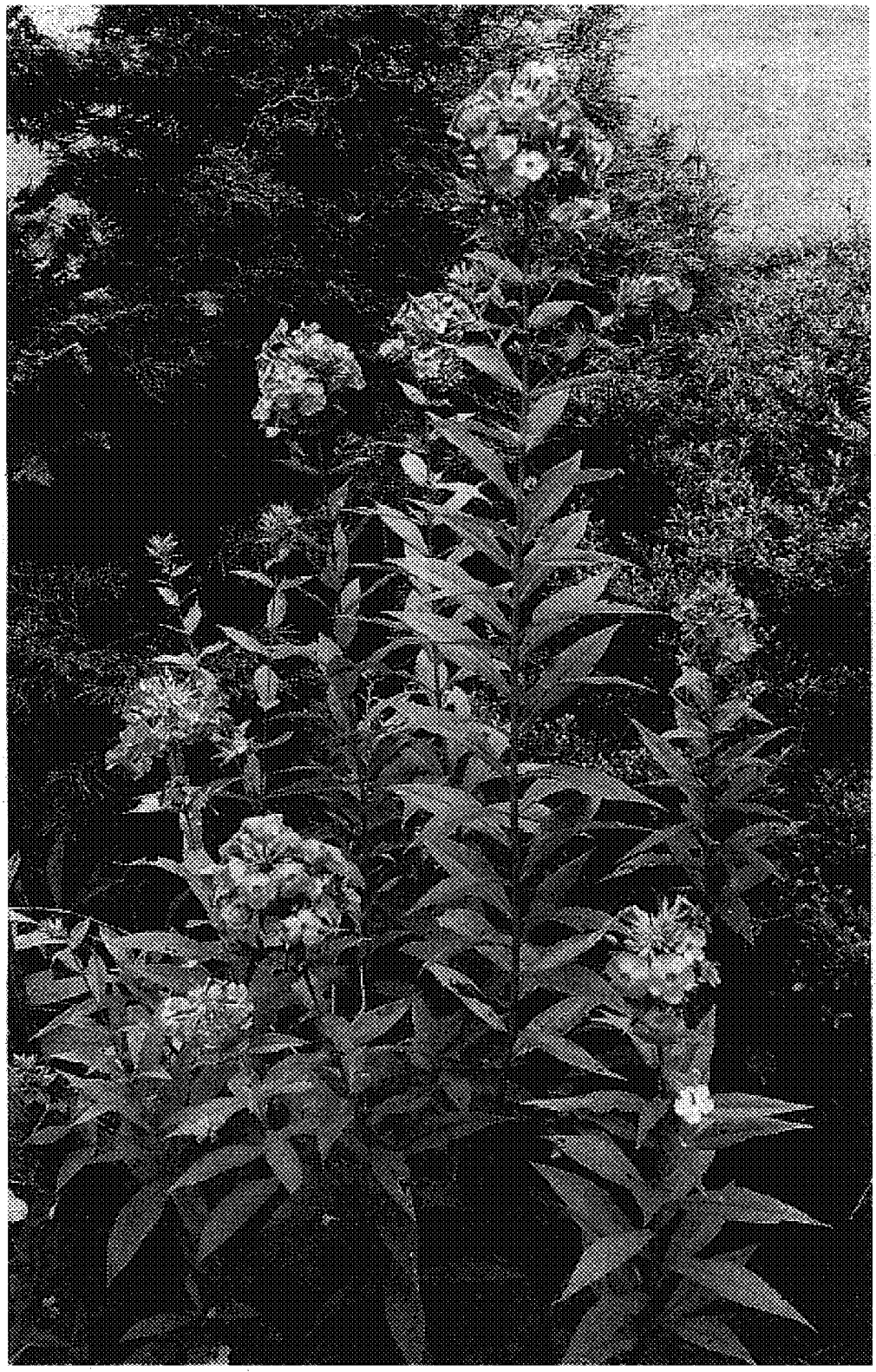

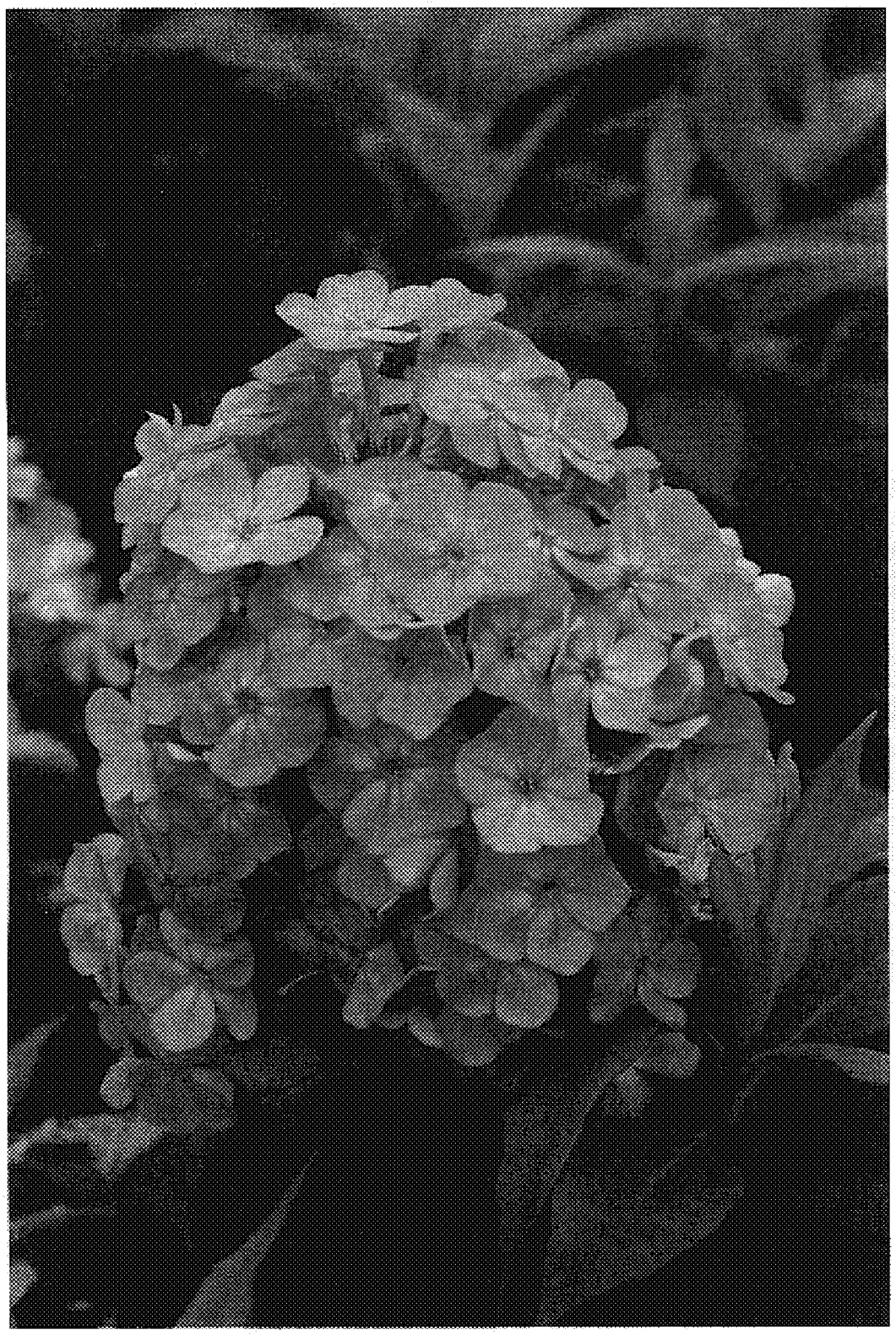

* * * * *